US005714689A

United States Patent [19]
Latimer et al.

[11] Patent Number: 5,714,689
[45] Date of Patent: Feb. 3, 1998

[54] ZIG ZAG ELECTROMAGNETIC ACOUSTIC TRANSDUCER SCAN

[75] Inventors: Paul J. Latimer; Daniel T. MacLauchlan, both of Lynchburg, Va.

[73] Assignee: The Babcock & Wilcox Company, New Orleans, La.

[21] Appl. No.: 842,402

[22] Filed: Apr. 24, 1997

Related U.S. Application Data

[63] Continuation of Ser. No. 653,809, May 28, 1996, abandoned, which is a continuation of Ser. No. 257,403, Jun. 9, 1994, abandoned.

[51] Int. Cl.$^6$ .................................................. G01N 29/20
[52] U.S. Cl. .................................. 73/600; 73/643; 73/618
[58] Field of Search ................................. 73/598, 600, 618, 73/641, 643, 599, 619, 633

[56] References Cited

U.S. PATENT DOCUMENTS

| | | | |
|---|---|---|---|
| 4,307,615 | 12/1981 | Robinson | 73/643 |
| 4,348,903 | 9/1982 | Sato et al. | 73/643 |
| 4,351,184 | 9/1982 | Garner et al. | 73/618 |
| 4,420,978 | 12/1983 | Robinson et al. | 73/643 |
| 4,699,007 | 10/1987 | Kawashima et al. | 73/641 |
| 4,793,185 | 12/1988 | Boettger et al. | 73/643 |
| 5,154,081 | 10/1992 | Thompson et al. | 73/643 |
| 5,299,458 | 4/1994 | Clark, Jr. et al. | 73/643 |

OTHER PUBLICATIONS

Proposed Statement of Work, submitted to J. Meacham Program Manager SP.7 Committee, Aug. 31, 1993.

Primary Examiner—Hezron E. Williams
Assistant Examiner—Nashmiya Ashraf
Attorney, Agent, or Firm—Daniel S. Kalka; Robert J. Edwards

[57] ABSTRACT

A flaw detection method and arrangement utilizes electromagnetic acoustic transducers (EMATs) which ultrasonically test a material for cracks or flaws. Four EMATs are used in a pitch-catch configuration, i.e. two pairs of EMAT transmitters and receivers. The EMAT transmitters and receivers are arranged such that a first EMAT transmitter is located on the surface diagonally across from a first EMAT receiver and a second EMAT transmitter is located diagonally across from a second EMAT receiver. The first and second EMAT transmitters transmit ultrasonic signals to the first and second EMAT receivers respectively; and these ultrasonic signals are transmitted orthogonal to each other. A pulser/receiver is operatively connected to the first and second EMAT transmitters and the first and second EMAT receivers for inducing the EMAT transmitters to propagate their respective waves. The pulser/receiver also receives the signal transmitted through the material after being received by the first and second EMAT receivers. A power source is operatively connected to the pulser/receiver for powering the arrangement; and a computer or oscillator is operatively connected to the pulser/receiver for recording and displaying the signals.

3 Claims, 3 Drawing Sheets

ZIG ZAG ELECTROMAGNETIC ACOUSTIC TRANSDUCER SCAN

This is a continuation of application Ser. No. 08/653,809 filed May 28, 1996, now abondoned, which is a continuation of application Ser. No. 08/257,403 filed Jun. 9, 1994, also now abondoned.

BACKGROUND OF THE INVENTION

1. Field of the Invention

The present invention relates, in general, to the detection of flaws in material and, in particular, to a new and useful arrangement and method for flaw detection in material using electromagnetic acoustic transducers (EMATs).

2. Description of the Related Art

Many methods are known for detecting flaws in various materials. The detection of surface breaking flaws has been performed for many years through the use of a liquid penetrant test (PT). In this process, the surface of the material is cleaned and the penetrant is then sprayed on the cleaned surface and allowed to penetrate into the cracks for a period of time. After the penetrant has had sufficient time to penetrate the cracks, excess penetrant is wiped off, and a developer is sprayed on the surface. The developer provides an outline of the crack. A major drawback to this process is that it requires judgment on behalf of the inspector which could lead to error. The tightness of the crack can have a decided effect upon the ability to detect the crack with this technique. Moreover, the entire process is slow, time consuming and costly. In addition, many government agencies have been classifying certain penetrants as hazardous materials.

Another technique that has been used for the detection of surface breaking flaws is a magnetic particle test (MT). The basis of the MT process is that a surface breaking flaw is a gap in an object that has been magnetized. Consequently, when iron powder is sprinkled over the object, the powder is magnetically attracted to the gap. When the excess powder is removed, an outline of the gap remains. This technique is also slow and relies largely upon the judgment of the operator.

Eddy currents have also been used for surface breaking flaw detection. Although it is known that eddy currents are useful for scanning complex geometries and small areas, their coverage is limited by the small size of most eddy current coils.

Additionally, conventional piezoelectric ultrasonic techniques have been used for the detection of surface breaking flaws. The usual technique involves the use of shear waves. Although surface waves are the most sensitive mode for detection of surface breaking flaws, surface waves cannot be efficiently generated with conventional ultrasonic sensors because of problems associated with the liquid required to couple the sound into the object being tested.

SUMMARY OF THE INVENTION

The present invention pertains to a flaw detection method and arrangement utilizing electromagnetic acoustic transducers (EMATs) which ultrasonically test a material for cracks or flaws.

The arrangement according to the present invention comprises a first EMAT transmitter which is placed on a surface of the material for ultrasonically transmitting a signal or wave through the material. A first EMAT receiver is placed on the surface of the material and spaced a distance away from the first EMAT transmitter for receiving the first ultrasonic signal transmitted through the material by the first EMAT transmitter. A second EMAT transmitter is placed on the surface of the material and ultrasonically transmits a second signal through the material to a second EMAT receiver placed on the material and spaced a distance away from the second EMAT transmitter. The EMAT transmitters and receivers are arranged such that the first EMAT transmitter is located on the surface diagonally across from the first EMAT receiver and the second EMAT transmitter is located diagonally across the second EMAT receiver. The first and second transmitted ultrasonic signals are transmitted orthogonal to each other. A pulser/receiver is operatively connected to the first and second EMAT transmitters and the first and second EMAT receivers for inducing the EMAT transmitters to propagate their respective waves. The pulser/receiver also receives the signal transmitted through the material after being received by the first and second EMAT receivers. A power source is operatively connected to the pulser/receiver for powering the arrangement; and a computer or oscilloscope is operatively connected to the pulser/receiver for recording and displaying the signals.

The method according to the present invention comprises linearly moving the first and second EMAT transmitters and the first and second EMAT receivers about the surface of the material for providing a zig-zag scan of the material in order to detect the presence and orientation of a flaw such as a crack.

The present invention also provides for an arrangement for use on a material having a narrow width wherein an EMAT transmitter is placed on the surface of the material and ultrasonically transmits a wave through the material to the edge of the material for deflecting the wave from the edge. This wave propagation can be a multiple reflection between edges of the material. An EMAT receiver is located on the surface of the material for receiving the reflected wave. Both the EMAT transmitter and receiver are linearly movable about the surface of the material for providing a zig-zag scan.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

The present invention utilizes EMATs which comprise EMAT coils, i.e. meander coils which are placed under respective magnets and oriented so that they generate sound waves, when activated or excited, that propagate into a material being tested or inspected.

Figure 1A:
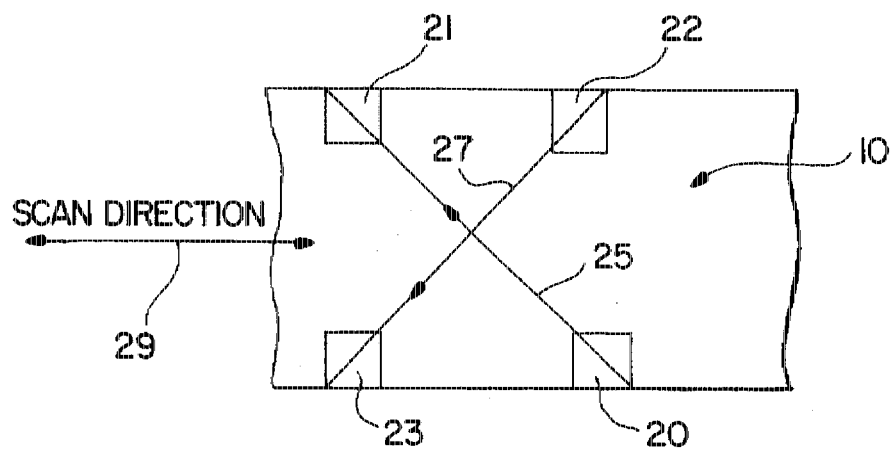
FIG. 1A is a schematic view illustrating a section of a first embodiment of an arrangement for scanning a material according to the present invention.
Figure 2:
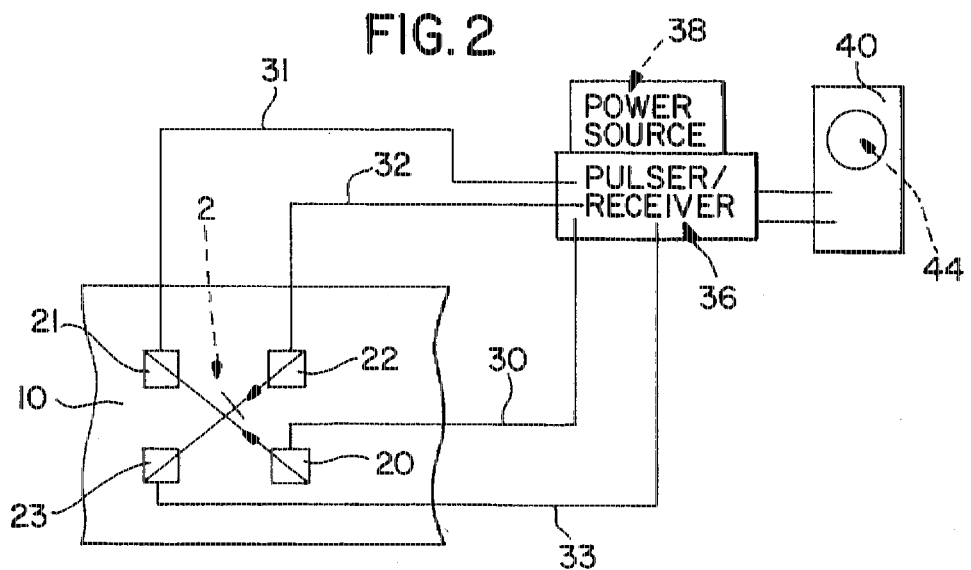
FIG. 2 is a schematic view illustrating the first embodiment of the arrangement for scanning a material according to the present invention.

FIG. 1A illustrates one embodiment for an arrangement of EMATs having a first EMAT transmitter 20 placed on the surface of a material 10 and a first EMAT receiver 21 diagonally spaced from the EMAT transmitter 20. EMAT transmitter 20 propagates a signal or wave 25 through the material 10 which is detected or sensed at EMAT receiver 21. A second EMAT transmitter 22 is positioned on the surface of the material 10 and a second EMAT receiver 23 is diagonally spaced across from the EMAT transmitter 22 for receiving a second propagated signal 27. The EMAT transmitters 20 and 22 and the EMAT receivers 21 and 23 are linearly movable on the surface of the material 10 in a scanning direction 29. By transmitting the ultrasonic waves 25 and 27 diagonally from one side of the material 10 to the other, and receiving the signals 25 and 27 at the EMAT receivers 21 and 23 respectively, surface cracks in the material 10 are detected with all orientations in the material 10. Preferably, the first propagated signal 25 is orthogonal to the second propagated signal 27. The arrangement of EMATs 20, 21, 22 and 23 illustrated in FIG. 1A is commonly known as a "pitch-catch" configuration. As shown in FIG. 2, the EMATs 20, 21, 22 and 23 are operatively connected to a pulser and receiver unit 36 by connectors such as wires 30, 31, 32 and 33 respectively. A power source 38 is operatively connected to the pulser/receiver 36 for powering the arrangement. A computer having recording and display capability 40, which can also be an oscilloscope, is operatively connected by wire 41 to the pulser/receiver 36 for recording and displaying the propagated signals transmitted and received by the EMATs 20, 21, 22 and 23 on the material 10, which are in turn, displayed on a display 44.

Because the EMATs 20, 21, 22 and 23 are linearly movable on the surface of material 10, a flaw 2 in the material 10 is easily detected with one linear scan which is a zig-zag scan. This method also allows for the detecting of all orientations of the flaw 2 with the signal scan.

As illustrated in FIGS. 1A and 2, a flaw 2 located between a pair of pitch-catch EMAT sensors 20 and 21 partially or totally blocks the ultrasonic beam 25 emitted by transmitter 20 which causes a loss of the signal 25. Therefore, by utilizing pitch-catch EMATs 22 and 23 such that ultrasonic beam 27 is propagated orthogonal to the ultrasonic beam 25, the arrangement of EMAT sensors 20, 21, are sensitive to any flaws aligned parallel to the beam 27. Due to this unique configuration, which is a propagation of ultrasonic waves in an "X" pattern, a maximum area of the material 10 is covered by a single linear scan. After conducting one linear scan by EMATs 20, 21, 22 and 23 over the material 10, an area equal to the length of scan times the perpendicular distance between the EMAT coils will have been inspected for all orientations on the surface breaking flaws 2 of the material 10.

Figure 1B:
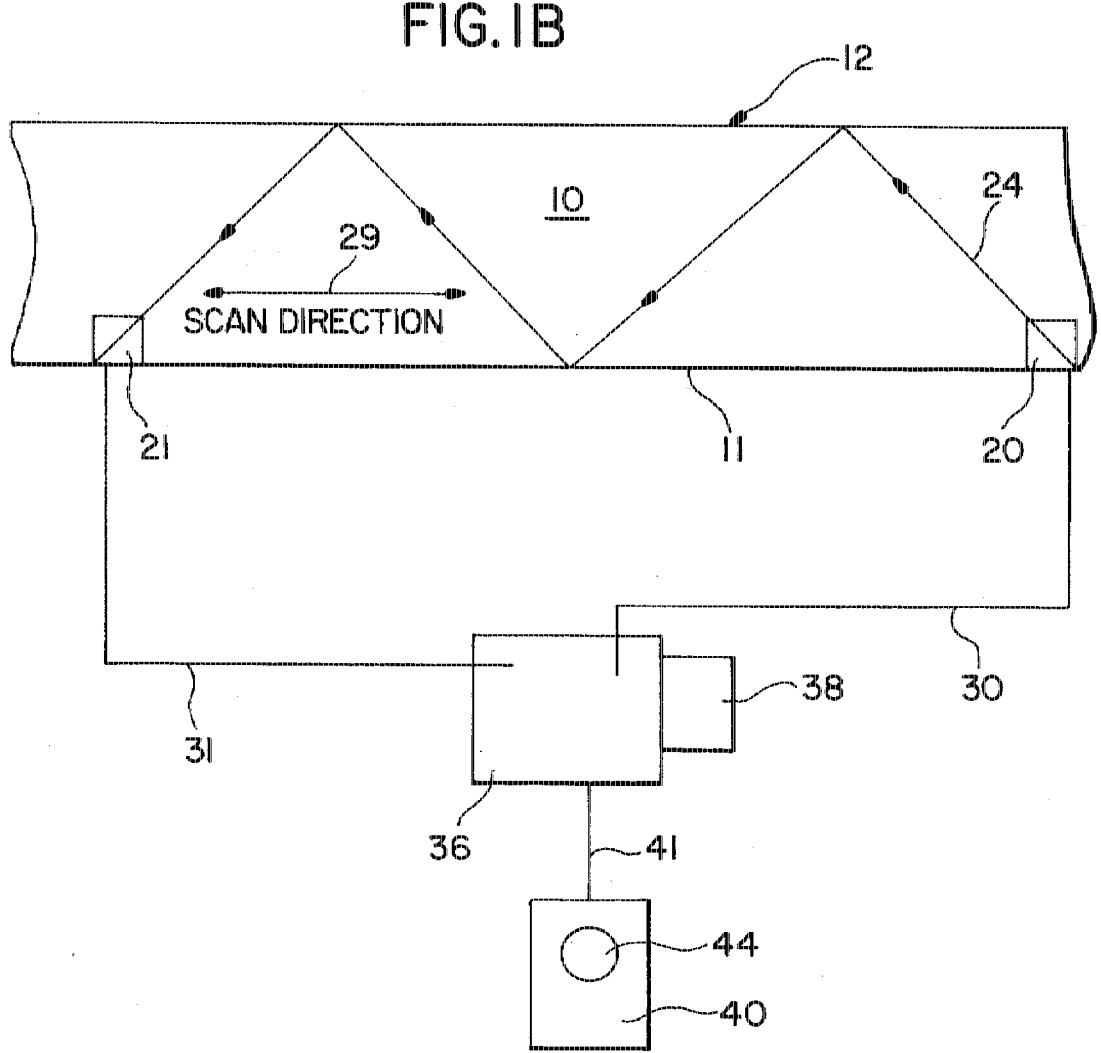
FIG. 1B is a schematic view illustrating a second embodiment of an arrangement for scanning a material according to the present invention.

FIG. 1B illustrates a second embodiment of the present invention which provides one EMAT transmitter 20 on the surface 10 and one EMAT receiver 21 on the surface 10 which can be located at or near edges 11 or 12 of the material 10 for permitting close inspection of the material 10 at edges 11 and 12 and other areas of the material 10 that are difficult to inspect. Ultrasonic wave 24 is propagated from EMAT transmitter 20 to edge 12, which in turn, is reflected from edge 12 to edge 11 and so-on until received by EMAT receiver 21. By linearly moving EMATs 20 and 21 in scanning direction 29 along the surface 10, any type of flaw and its orientation can be detected. This arrangement is useful for narrow strips of material or material having narrow widths. The transmission and reception of wave 24, as well as the recording and display thereof, is conducted in the same fashion as the embodiment illustrated in FIG. 2, i.e. through the use of pulser/receiver 36, power source 38, wires 30 and 31, computer/oscilloscope 40, with display 44 and wire 41.

The separation of the array of sensors 20 and 21 can be changed in order to change the width of the inspection band from very short distances up to 1 to 2 feet.

Figure 4:
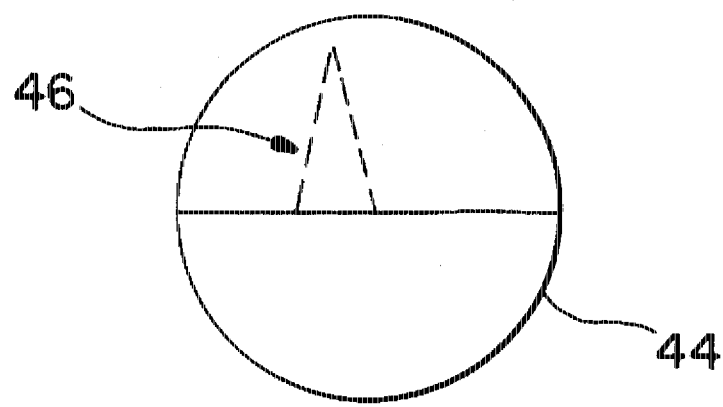
FIG. 4 is a view illustrating a display showing a signal indicating no flaw.
Figure 5:
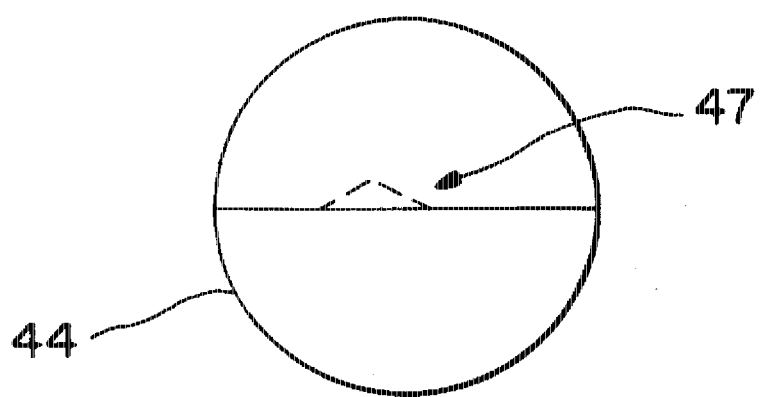
FIG. 5 is a view illustrating a display showing a signal indicating a flaw.

When a flaw 2 (FIG. 2) is detected, a signal 47, which indicates the presence of a flaw, is displayed on display 44 of oscilloscope 40 as shown in FIG. 5. When no flaw has been detected, a signal 46 indicating this is displayed on display 44 as illustrated in FIG. 4.

The frequency for waves 25 and 27 (FIGS. 1A and 2) and 24 (FIG. 1B) can be chosen to correspond to any desired depth of penetration. For Rayleigh waves, the depth of penetration is approximately one wavelength. Therefore, a two MMz EMAT has a depth of penetration depth of 0.060" and a one MHz EMAT has a depth of penetration of 0.12", etc.

The EMATs used in the present invention have meander coils wherein the period of the coil, i.e. twice the distance separating adjacent conductors, is equal to the wavelength of the ultrasonic wave. For low temperature operation, the EMAT coils are typically flexible printed circuits covered with high molecular weight polyethylene. For high temperature applications, the EMAT coils are heat resistant and are constructed of a ceramic coated wire.

Figure 3:
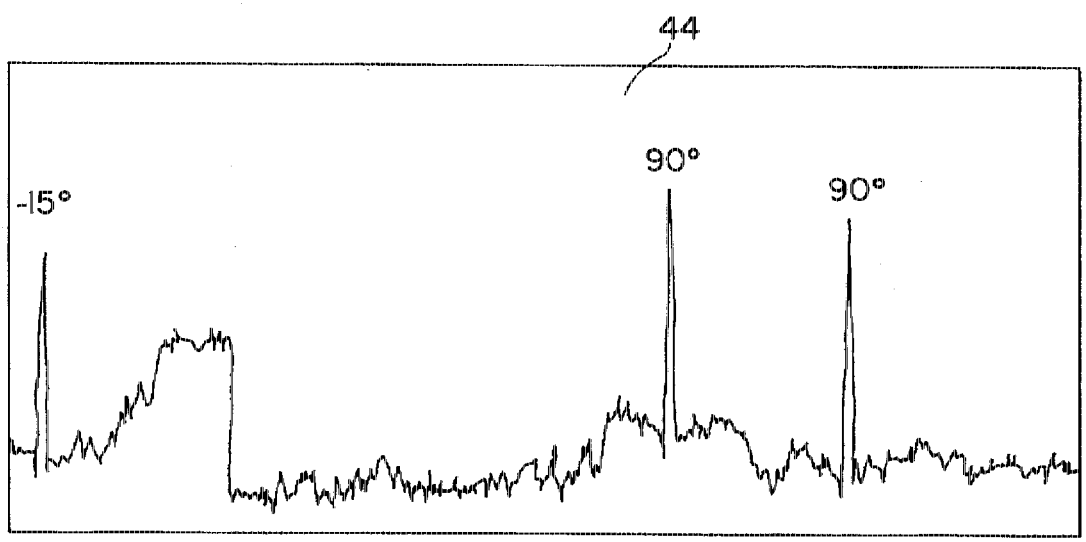
FIG. 3 is a chart showing a recorded signal for the present invention.

A permanent record of the indication is easily obtained using a strip chart recorder or a computer 40 with any other suitable data acquisition system similar to the strip chart 44 such as shown in FIG. 3. In addition, the instrumentation, such as that shown in FIG. 2, can be provided with audio and visual alarms to alert the operator of the presence of a flaw 2 in real time.

Experimental results of the present invention were confirmed in the laboratory using permanent magnets of two MHz meander coil EMATs. The flaw was a notch with dimensions 0.125" L×0.035" D in aluminum. The results are shown on the strip chart recording display 44 in FIG. 3. Note that the response has been inverted to show a positive spike for an attenuated signal. In FIG. 3, the small area where the baseline is raised corresponds to the position where the sensor was removed from the plate and then positioned again on the aluminum plate. The excellent signal to noise ratio demonstrates the success of the present invention. The scans were performed with the flaw orientations at 90° and 45°.

Advantages of the present invention include the following: the surface waves of the present invention provide one of the most sensitive methods of detecting surface breaking flaws; EMATs used by the present invention are much more efficient at producing surface waves than conventional ultrasonics because no couplant is required; the present invention does not depend upon operator judgment as with magnetic particle (MT) and penetrant tests (PT); the present invention allows all flaw orientations to be detected with one linear scan; the present invention provides a scanning speed which is rapid; no environmental problems due to hazardous chemical use are associated with the present invention; the scan band or width of coverage can be varied; the penetration depth of the surface waves can be changed by changing the frequency; and the present invention can be easily automated for assembly line or robotic inspections.

While specific embodiments of the invention have been shown and described in detail to illustrate the application of the principles of the invention, it will be understood that the invention may be embodied otherwise without departing from such principles.

What is claimed is:

1. An arrangement for detecting a presence and an orientation of a surface breaking flaw in a material, the arrangement comprising:

first electromagnetic acoustic transmitter means positioned on a surface of the material for ultrasonically transmitting a first ultrasonic surface wave through the material;

first electromagnetic acoustic receiver means positioned on the surface of the material for receiving the first ultrasonic surface wave transmitted by the first electromagnetic acoustic transmitter means, the first electromagnetic acoustic receiver means being spaced in a diagonal direction with respect to the first electromagnetic acoustic transmitter means a distance away from the first electromagnetic acoustic transmitter means;

second electromagnetic acoustic transmitter means positioned on the surface of the material for ultrasonically transmitting a second ultrasonic surface wave through the material;

second electromagnetic acoustic receiver means positioned on the surface of the material for receiving the second ultrasonic surface wave transmitted by the second electromagnetic acoustic transmitter means, the second electromagnetic acoustic receiver means being spaced in a diagonal direction with respect to the second electromagnetic acoustic transmitter means a distance away from the second electromagnetic acoustic transmitter means, the first ultrasonic surface wave being transmitted between the first electromagnetic acoustic transmitter and receiver orthogonal to the second ultrasonic surface wave transmitted between the second electromagnetic acoustic transmitter and receiver for propagation of the first ultrasonic surface wave and the second ultrasonic surface wave in an X pattern, the first and second electromagnetic acoustic transmitter means and the first and second electromagnetic acoustic receiver means including means for linearly scanning the surface of the material;

pulser and receiver means operatively connected to the first and second electromagnetic acoustic transmitter means and to the first and second electromagnetic acoustic receiver means for inducing a transmission of the first ultrasonic surface wave and the second ultrasonic surface wave and for receiving the first ultrasonic surface wave and the second ultrasonic surface wave received by the first and second electromagnetic receiver means;

means for powering the arrangement; and display means operatively connected to the pulser and receiver means for displaying the first ultrasonic surface wave and second ultrasonic surface wave transmitted by the first and second electromagnetic acoustic transmitter means and received by the first and second electromagnetic acoustic receiver means for detecting a presence and an orientation of a surface breaking flaw in the material through an attenuated signal in the displayed signal from the first ultrasonic surface wave and the second ultrasonic surface wave.

2. A method for detecting a presence and an orientation of a surface breaking flaw in a material, the method comprising the steps of:

placing first electromagnetic acoustic transmitter means on a surface of the material;

placing first electromagnetic acoustic receiver means on the surface of the material spaced in a diagonal direction with respect to the first electromagnetic acoustic transmitter means a distance away from the first electromagnetic acoustic transmitter means;

placing second electromagnetic acoustic transmitter means on the surface of the material;

placing second electromagnetic acoustic receiver means on the surface of the material spaced in a diagonal direction with respect to the second electromagnetic acoustic transmitter means a distance away from the second electromagnetic acoustic transmitter means;

inducing the first electromagnetic acoustic transmitter means to transmit a first ultrasonic surface wave to be received by the first electromagnetic acoustic receiver means;

inducing the second electromagnetic acoustic receiver means to transmit a second ultrasonic surface wave through the material to be received by the second electromagnetic acoustic receiver means, the first ultrasonic surface wave being propagated in a direction orthogonal to the second ultrasonic surface wave;

propagating said first and second ultrasonic waves in an X pattern;

linearly scanning the surface of the material with the first and second electromagnetic acoustic transmitter means and the first and second electromagnetic acoustic receiver means; and monitoring the first ultrasonic surface wave and the second ultrasonic surface wave for attenuated signal for detecting a presence and an orientation of a surface breaking flaw in the material.

3. The method according to claim 2, further comprising the step of displaying the first and second ultrasonic waves transmitted and received.

* * * * *